United States Patent
Simmers

(10) Patent No.: US 9,782,574 B2
(45) Date of Patent: Oct. 10, 2017

(54) FORCE-CONTROLLED APPLICATOR FOR APPLYING A MICRONEEDLE DEVICE TO SKIN

(71) Applicant: 3M INNOVATIVE PROPERTIES COMPANY, St. Paul, MN (US)

(72) Inventor: Ryan P. Simmers, Fargo, ND (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 14/433,208

(22) PCT Filed: Oct. 7, 2013

(86) PCT No.: PCT/US2013/063611
§ 371 (c)(1),
(2) Date: Apr. 2, 2015

(87) PCT Pub. No.: WO2014/058746
PCT Pub. Date: Apr. 17, 2014

(65) Prior Publication Data
US 2015/0258319 A1    Sep. 17, 2015

Related U.S. Application Data

(60) Provisional application No. 61/712,050, filed on Oct. 10, 2012.

(51) Int. Cl.
*A61M 37/00* (2006.01)

(52) U.S. Cl.
CPC . *A61M 37/0015* (2013.01); *A61M 2037/0023* (2013.01); *A61M 2037/0046* (2013.01); *A61M 2037/0061* (2013.01)

(58) Field of Classification Search
CPC ...... A61M 37/0015; A61M 2037/0061; A61M 2037/0023; A61M 2037/0046
See application file for complete search history.

(56) References Cited

U.S. PATENT DOCUMENTS

| 4,751,087 A | 6/1988 | Wick |
| 4,834,979 A | 5/1989 | Gale |

(Continued)

FOREIGN PATENT DOCUMENTS

| WO | WO 2007-124411 | 11/2007 |
| WO | WO 2011-115602 | 9/2011 |

(Continued)

OTHER PUBLICATIONS

International Search Report for PCT International Application No. PCT/US2013/063611, mailed on Jan. 17, 2014, 6pgs.

*Primary Examiner* — Theodore Stigell
*Assistant Examiner* — Amber Stiles
(74) *Attorney, Agent, or Firm* — 3M Innovative Properties Company; Eric E. Silverman

(57) ABSTRACT

An applicator (100) for applying a microneedle device to a skin surface. The applicator can include a microneedle device (106), a housing (102), and a connecting member (110). The connecting member can be configured to allow the microneedle device to move between: (i) a first position in which at least a portion of the microneedle device extends beyond the housing; and (ii) a second position in which the microneedle device is recessed within the housing when a threshold application force is applied to the microneedle device in a direction substantially perpendicular with respect to the microneedle device.

20 Claims, 3 Drawing Sheets

(56) References Cited

U.S. PATENT DOCUMENTS

| | | |
|---|---|---|
| 5,688,523 A | 11/1997 | Garbe |
| 6,004,578 A | 12/1999 | Lee |
| 6,024,976 A | 2/2000 | Miranda |
| 6,091,975 A | 7/2000 | Daddona |
| 6,149,935 A | 11/2000 | Chiang |
| 6,312,612 B1 | 11/2001 | Sherman |
| 6,365,178 B1 | 4/2002 | Venkateshwaran |
| 6,379,324 B1 | 4/2002 | Gartstein |
| 6,537,242 B1 | 3/2003 | Palmer |
| 6,558,361 B1 | 5/2003 | Yeshurun |
| 6,855,131 B2 | 2/2005 | Trautman |
| 7,648,484 B2 | 1/2010 | Yeshurun |
| 2003/0054025 A1 | 3/2003 | Cantor |
| 2004/0049150 A1 | 3/2004 | Dalton |
| 2005/0096586 A1 | 5/2005 | Trautman |
| 2005/0261631 A1 | 11/2005 | Clarke |
| 2006/0095061 A1 | 5/2006 | Trautman |
| 2007/0185515 A1 | 8/2007 | Stout |
| 2008/0009811 A1* | 1/2008 | Cantor ................. A61B 17/205 604/272 |
| 2008/0108958 A1 | 5/2008 | Carter |
| 2008/0114298 A1 | 5/2008 | Cantor |
| 2008/0183144 A1 | 7/2008 | Trautman |
| 2008/0195035 A1 | 8/2008 | Frederickson |
| 2009/0198189 A1* | 8/2009 | Simons ............ A61M 37/0015 604/173 |
| 2010/0179473 A1* | 7/2010 | Genosar ............ A61M 5/14248 604/70 |
| 2011/0213335 A1 | 9/2011 | Burton |
| 2011/0276027 A1 | 11/2011 | Trautman |
| 2012/0123387 A1 | 5/2012 | Gonzalez |

FOREIGN PATENT DOCUMENTS

| | | |
|---|---|---|
| WO | WO 2012-074576 | 6/2012 |
| WO | WO 2012-122162 | 9/2012 |
| WO | WO 2013-055638 | 4/2013 |
| WO | WO 2013-055641 | 4/2013 |

\* cited by examiner

FORCE-CONTROLLED APPLICATOR FOR APPLYING A MICRONEEDLE DEVICE TO SKIN

CROSS REFERENCE TO RELATED APPLICATIONS

This is a national stage filing under 35 U.S.C. §371 of PCT/US2013/063611, filed Oct. 7, 2013, which claims priority to U.S. Provisional Application No. 61/712,050, filed Oct. 10, 2012, the disclosure of which is incorporated herein by reference in its entirety.

FIELD

The present disclosure generally relates to applicators and methods for applying a microneedle device to skin to treat an area of the skin and/or deliver an active agent to the skin.

BACKGROUND

Transdermal and topical drug delivery can be used for therapeutic treatment, but the number of molecules that can be effectively delivered using these routes can be limited by the barrier properties of skin. The main barrier to transport of molecules through the skin is the stratum corneum (the outermost layer of the skin).

A number of different skin treatment methods have been proposed in order to increase the permeability or porosity of the outermost skin layers, such as the stratum corneum, thus enhancing drug delivery through or into those layers. The stratum corneum is a complex structure of compact keratinized cell remnants separated by lipid domains. The stratum corneum is formed of keratinocytes, which comprise the majority of epidermal cells, that lose their nuclei and become corneocytes. These dead cells comprise the stratum corneum, which has a thickness of only about 10-30 microns and protects the body from invasion by exogenous substances and the outward migration of endogenous fluids and dissolved molecules. Various skin treatment methods include the use of microneedles, laser ablation, RF ablation, heat ablation, sonophoresis, iontophoresis, or a combination thereof.

Devices including arrays of relatively small structures, sometimes referred to as microneedles or micro-pins, have been disclosed for use in connection with the delivery of therapeutic agents and other substances through the skin and other surfaces. The devices are typically pressed against the skin in an effort to pierce the stratum corneum such that the therapeutic agents and other substances can sequentially or simultaneously pass through that layer and into the tissues below. Microneedles of these devices pierce the stratum corneum upon contact, making a plurality of microscopic slits which serve as passageways through which molecules of active components can be delivered into the body. In delivering an active component, the microneedle device can be provided with a reservoir for temporarily retaining an active component in liquid form prior to delivering the active component through the stratum corneum. In some constructions, the microneedles can be hollow to provide a liquid flow path directly from the reservoir and through the microneedles to enable delivery of the therapeutic substance through the skin. In alternate constructions, active component(s) may be coated on the microneedle array and delivered directly through the skin after the stratum corneum has been punctured.

In some cases, microneedle arrays can be used in conjunction with an applicator device capable of being used several times or as a single-use device. The microneedle arrays are generally used once and then discarded.

Issues related to applying microneedles include the ability to effectively and consistently insert the needles to a desired depth in the skin, as well as the ability to limit the maximum amount of application force that may be applied to a skin surface during treatment.

SUMMARY

The present disclosure relates to applicators that can be used to treat a selected site (e.g., on skin), and/or to apply an active ingredient to the treated site. One feature and advantage of applicators of the present disclosure is that they can achieve a desired depth of penetration (e.g., by achieving a minimum application force) and can limit the amount of force that can be applied to a microneedle device and to skin, for example, by causing the microneedle device to retract after a maximum application force has been met. Applicators of the present disclosure can be configured to deliver a range of forces (e.g., from a minimum required to achieve a desired depth of penetration to a maximum required to limit pain and/or depth of penetration) to achieve a desired depth of penetration range. As a result, even if the applicator itself is continued to be pressed onto the skin, the microneedles will no longer be puncturing the skin and will have been removed from the skin surface when the maximum application force was achieved.

In some embodiments, applicators of the present disclosure can be used to treat (e.g., perforate) skin with microneedles (e.g., uncoated microneedles) to create microchannels in the skin. Generally, targeted penetration of the microneedles includes penetration into the epidermis and dermis of the skin. In some embodiments, an active agent (e.g., a drug) can be coated on the microneedles, such that the active agent is delivered into the skin (e.g., into the epidermis and possibly the dermis) when the microneedles puncture the skin. In some embodiments, applicators of the present disclosure can be used to "pre-treat" skin with microneedles (e.g., coated or uncoated) for subsequent application of an active over the treated site. The active agent can be applied by applying a transdermal patch comprising the active agent over the treated site, or in some embodiments, a lotion, cream, gel, ointment, or the like, can be applied over the treated site. Still, in some embodiments, an active agent can be applied topically to skin (e.g., in the form of a lotion, cream, gel, ointment, or the like), and the applicator can be used to apply the microneedles (e.g., uncoated or coated) to the skin after topical application of the active agent. In some embodiments, a combination of any of the above application or treatment techniques can be performed using applicators of the present disclosure.

Some aspects of the present disclosure provide an applicator for applying a microneedle device to a skin surface. The applicator can include a microneedle device having a first side comprising a microneedle array and a second side opposite the first side. The first side of the microneedle device can be configured to be positioned toward the skin surface. The applicator can further include a housing having a first surface configured to be positioned toward the skin surface, and a connecting member positioned to couple the microneedle device to the housing. The connecting member can be configured to allow the microneedle device to move relative to the housing between: (i) a first position in which at least a portion of the microneedle device extends beyond the first surface of the housing; and (ii) a second position in which the microneedle device is recessed within the housing, such that the microneedle device does not extend beyond the first surface of the housing; wherein the first surface of the housing is not in contact with the skin surface when the microneedle device is in the first position. The connecting member can be configured to move the microneedle device to the second position when a threshold application force is applied to the first side of the microneedle device in a direction substantially perpendicular with respect to the microneedle device.

Some aspects of the present disclosure provide a method of applying a microneedle device to a skin surface. The method can include providing the above applicator; pressing the applicator in a direction substantially perpendicular to the microneedle device into the skin surface when the microneedle device is in the first position until the threshold application force is met or exceeded; and moving the microneedle device to the second position in response to meeting or exceeding the threshold application force.

Other features and aspects of the present disclosure will become apparent by consideration of the detailed description and accompanying drawings.

DETAILED DESCRIPTION

Figure 1:
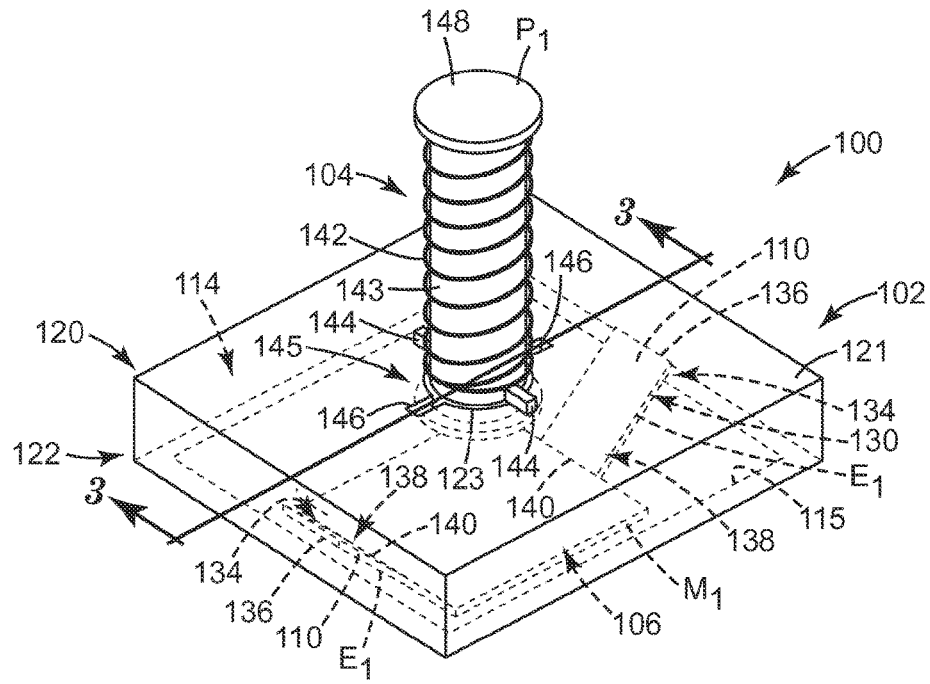
FIG. 1 is a top perspective view of an applicator according to one embodiment of the present disclosure, the applicator comprising a plunger and a microneedle device, the applicator shown with the microneedle device in a first position.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the term "coupled" and variations thereof are used broadly and encompass both direct and indirect couplings.

Further, "connected" and "coupled" are not restricted to physical or mechanical connections or couplings. It is to be understood that other embodiments may be utilized, and structural or logical changes may be made without departing from the scope of the present disclosure. Furthermore, terms such as "top," "bottom," "upper," "lower," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to an applicator and method for applying a microneedle device, comprising an array of microneedles, to skin (or a biological membrane) to treat the skin (i.e., create small holes or perforations or micropores in the skin) and/or to deliver an active agent to the skin. Particularly, applicators of the present disclosure can be configured such that the microneedles are removed from the skin and/or that a microneedle device comprising the microneedles is retracted when a threshold (e.g., maximum) application force has been achieved. When the applicator is applied to the skin, the microneedle device can be in its treatment position and state such that the microneedles penetrate the skin, and when a threshold (e.g., maximum) application force is achieved, the microneedle device can be retracted away from the skin (and, in some embodiments, into a cavity of the applicator) to a non-treatment position and state, such that the microneedles are no longer penetrating the skin. If the applicator is continued to be pressed onto the skin, the microneedles will no longer be in contact with or penetrating the skin. In some existing cases, a mechanical device or tool can be used to treat skin with microneedles at a precisely-controlled velocity and to a precisely-controlled depth of penetration. However, the applicators of the present disclosure can allow microneedles to be applied by hand (i.e., without requiring an additional mechanical device or tool) in a force-controlled manner. As a result, even inexperienced users applying the applicators of the present disclosure by hand will be inhibited from applying too great of an application force to the skin with the microneedle array, because the applicator will retract the microneedles from the skin when the maximum application force (and, accordingly, the desired depth of penetration) is achieved. The applicators of the present disclosure therefore provide a simple, low-cost and robust solution for applying microneedles to skin (e.g., using hand pressure) while controlling the depth of penetration and the maximum application force.

While some existing applicators and microneedle arrays are designed to be left in place on the skin, continuing to puncture the skin and/or deliver an active agent, the applicators of the present disclosure are designed to allow the microneedles to puncture the skin up to a desired force and to a desired depth, but are generally not designed to be left on the skin for an extended treatment period. On the contrary, even if the applicators of the present disclosure were left on the skin, the microneedles would no longer be puncturing the skin after the threshold application force had been met and the microneedles had been retracted away from the skin.

Some existing applicators require a specific application velocity of the microneedles to puncture skin. With applicators of the present disclosure, generally a gentle hand pressure is sufficient to achieve the desired depth of penetration, while also limiting the maximum application force that can be applied with the microneedles.

As mentioned above, applicators of the present disclosure may be useful when applied to the skin as a "pretreatment" step, that is, when applied to the skin to disrupt the stratum corneum layer of skin and then removed. The disrupted area of skin may then be useful for allowing enhanced delivery of a topical composition (e.g., a solution, a cream, a lotion, a gel, an ointment, or the like) or patch comprising an active agent that is applied to the disrupted area. Applicators of the present disclosure may also be useful when the microneedles are provided with a dried coating comprising an active agent that dissolved from the microneedles after they are inserted into the skin. As a result, applicators of the present disclosure may have utility for enhancing delivery of molecules to the skin, such as in dermatological treatments, vaccine delivery, or in enhancing immune response of vaccine adjuvants. As mentioned above, in some embodiments, the active agent may be applied to the skin (e.g., in the form of a solution that is swabbed onto the skin surface, or as a cream, lotion, gel, ointment, or the like, that is rubbed into the skin surface) prior to applying the microneedles of the applicators of the present disclosure.

When a patch is applied to the treated or disrupted site, the patch can be provided in a variety of forms and can include a drug reservoir comprising an active agent for delivery to the treated site. Any transdermal patch suitable for the continuous transdermal delivery of a therapeutically effective amount of an appropriate medicament may be used. Suitable transdermal patches include gelled or liquid reservoirs, such as in U.S. Pat. No. 4,834,979 (Gale), so-called "reservoir" patches; patches containing matrix reservoirs attached to the skin by an adjacent adhesive layer, such as in U.S. Pat. No. 6,004,578 (Lee et al.), so-called "matrix" patches; and patches containing pressure-sensitive adhesive (PSA) reservoirs, such as in U.S. Pat. No. 6,365,178 (Venkateshwaran et al.), U.S. Pat. No. 6,024,976 (Miranda et al.), U.S. Pat. No. 4,751,087 (Wick) and U.S. Pat. No. 6,149,935 (Chiang et al.), so-called "drug-in-adhesive" patches, the disclosures of which are hereby incorporated by reference. In some embodiments, the drug reservoir can be provided in the form of a matrix layer containing drug, the matrix layer being adhered to a skin-contact adhesive of the patch. Such a matrix may be an adhesive layer. Alternatively the matrix layer may be non-adhesive or weakly adhesive and rely upon the surrounding rim of skin-contact adhesive on an adhesive patch to secure the patch in place and keep the drug reservoir in contact with the skin surface.

In another embodiment, the drug reservoir can be provided in the form of solid particles embedded on the surface or within the skin-contact adhesive of the patch. In particular, these particles may be hydrophilic, so that contact with aqueous fluid exposed at the surface of the treated skin will cause them to dissolve or disintegrate, thus releasing drug into the skin.

In another embodiment, the drug reservoir can be provided within the skin-contact adhesive of the patch. The drug may be mixed with the skin-contact adhesive prior to forming the patch or it may be applied to the skin-contact adhesive of the patch in a separate process step. Examples of suitable methods for applying drug to an adhesive layer may be found in U.S. Patent Application Publication No. 2003/054025 (Cantor et al.) and U.S. Pat. No. 5,688,523 (Garbe et al.), the disclosures of which are hereby incorporated by reference.

The length of time between (i) treatment of the skin with microneedles to increase permeability and (ii) placement of the active agent in contact with the treated skin area may vary. In one embodiment, this length of time can be kept to a minimum in order to avoid any possibility of the skin barrier reforming through a healing process. The minimum length of time can be generally governed by the time it takes to remove the applicators of the present disclosure from the skin and apply the active agent, for example, by swapping on a solution, rubbing in a cream or lotion, remove the liner of a patch and applying its adhesive over the treated site (e.g., if a patch is being employed), etc. This time may be less than about 1 minute, less than about 30 seconds, less than about 10 seconds, or less than about 5 seconds. There is no reason, however, that this time cannot be extended to many minutes or hours if so desired. It is generally known that the length of time that the skin will remain increasingly permeable after treatment depends on the type of treatment and whether the skin is occluded or not after treatment. In some instances, increased permeability can be maintained for up to several days as long as the treated site remains occluded and even in the absence of occlusion the skin may have increased permeability for up to several hours. Thus, if it presented some convenience or clinical benefit, one could treat the site and delay drug delivery by wearing some type of dressing over the treated site until such time as one desired to begin drug delivery, at which time the active agent could be applied to the treated skin.

In discussing the applicators of the present disclosure, the term "downward," and variations thereof, is sometimes used to describe the direction in which microneedles are pressed into skin, and "upward" to describe the opposite direction. However, those of skill in the art will understand that the applicators can be used where the microneedles are pressed into skin at an angle to the direction of the earth's gravity, or even in a direction contrary to that of the earth's gravity, and these terms are only used for simplicity and clarity to describe relative directions.

Figure 2:
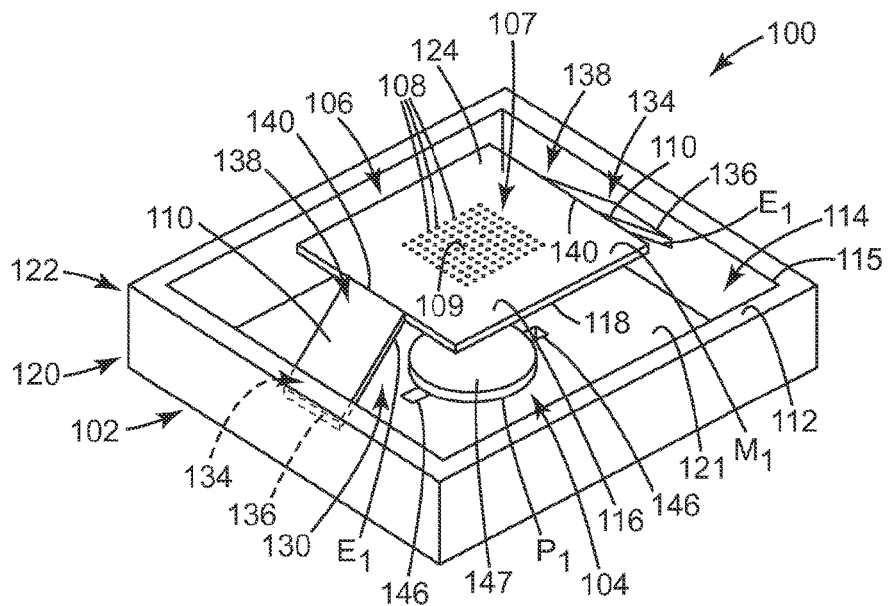
FIG. 2 is a bottom perspective view of the applicator of FIG. 1, the applicator shown with the microneedle device in the first position.
Figure 3:
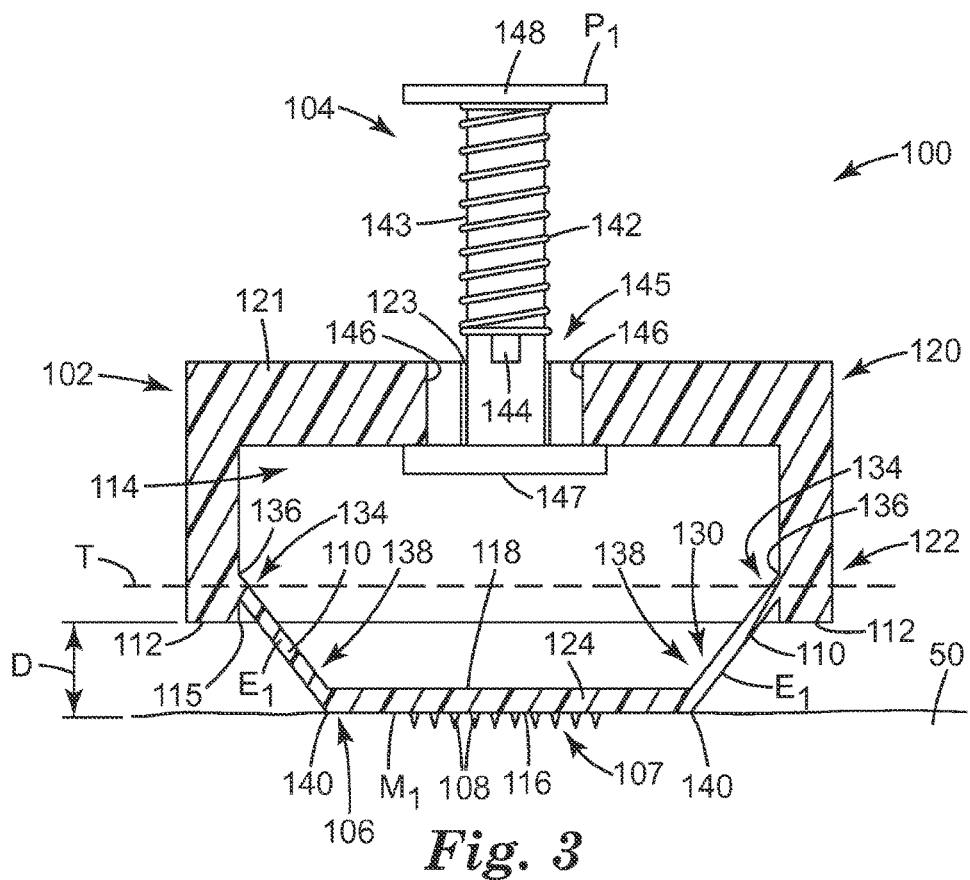
FIG. 3 is a side cross-sectional view of the applicator of FIGS. 1 and 2, taken along line 3-3 of FIG. 1, the applicator shown as it is being applied to a skin surface, with the microneedle device in the first position and microneedles of the microneedle device penetrating the skin.
Figure 4:
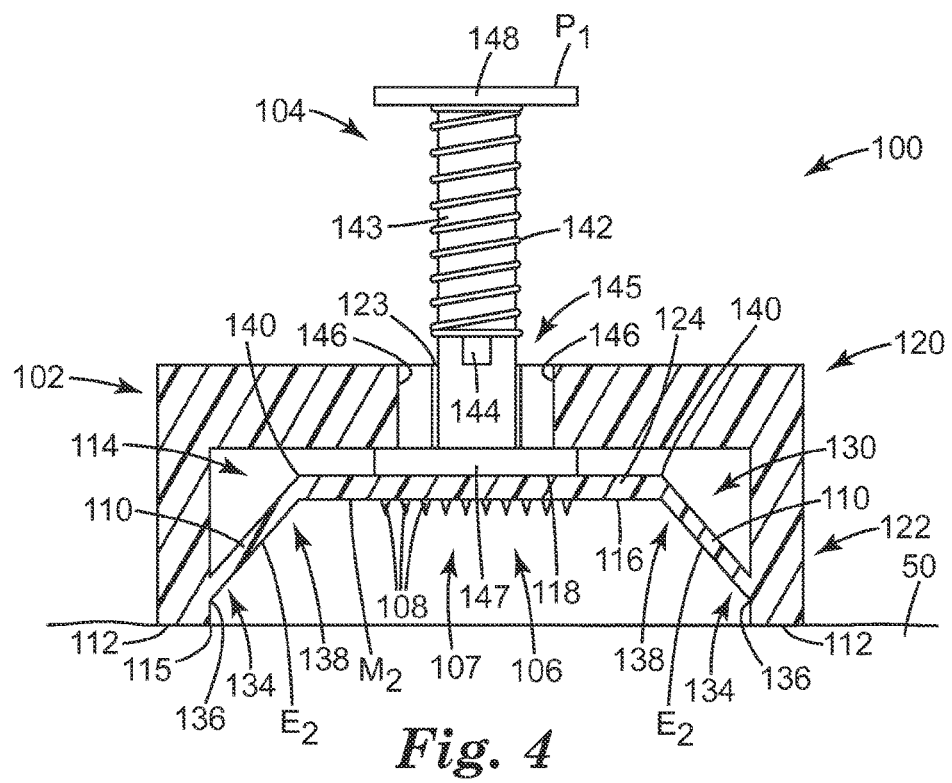
FIG. 4 is a side cross-sectional view of the applicator of FIGS. 1-3, taken along line 3-3 of FIG. 1, the applicator shown with the microneedle device in a second position in which the microneedles are no longer penetrating the skin.

FIGS. 1-5 illustrate an applicator 100 according to one embodiment of the present disclosure. FIGS. 1-3 and 5 show the applicator 100 in a first (or primed or treatment) state, and FIG. 4 show the applicator 100 in a second (or recessed or non-treatment) state. FIG. 4 shows the applicator 100 being applied to skin, or a skin surface, 50.

The applicator 100 can include a housing 102, a plunger (or piston, or actuator) 104, and a microneedle device 106 (comprising an array 107 of microneedles 108). The applicator 100 can further include one or more connecting members 110 positioned to couple the microneedle device 106 to the housing 102 and configured to allow the microneedle device 106 to move relative to the housing 102, for example, when an application force directed substantially perpendicularly with respect to the microneedle device 106 is applied to the microneedle device 106.

In some embodiments, the microneedles 108 can be configured to treat skin (i.e., create small holes or perforations or micropores in the skin) and/or deliver an active agent via skin, particularly, mammalian skin, and particularly, transdermally. Various microneedles that can be employed in applicators and methods of the present disclosure are described in greater detail below.

The term "transdermally," and variations thereof, is generally used to refer to any type of delivery of an active ingredient that crosses any portion of skin. That is, transdermally can generally include systemic delivery (i.e., where the active ingredient is transported across, or substantially through, the dermis such that the active ingredient is delivered into the bloodstream), as well as intradermal delivery (i.e., where the active ingredient is transported partially through the dermis, e.g., across the outer layer (stratum corneum) of the skin, where the active ingredient is delivered into the skin, e.g., for treating psoriasis or for local anesthetic delivery). That is, transdermal delivery as used herein includes delivery of an active ingredient that is transported across at least a portion of skin (but not necessarily all of the layers of skin), rather than merely being topically applied to an outer layer of the skin.

The "microneedle device" 106 can also be referred to as a "microneedle array assembly" and can include the array 107 of microneedles 108 (or, collectively, the "microneedle array" 107) and any supporting structure or substrate used to support the microneedle array 107 and/or to couple the microneedle array 107 to other structures or components of the applicator 100. For example, in some embodiments, the "microneedle device" or "microneedle array assembly" 106 can refer to the microneedle array 107, and a carrier (or "array carrier" or "substrate") 124. In the embodiment illustrated in FIGS. 1-5, the microneedles 108 are formed in or directly coupled to the carrier 124. However, it should be understood that additional layers can be coupled between the illustrated carrier 124 and the microneedle array 107. For example, in some embodiments, the microneedle array 107 can be formed in or directly coupled to a first carrier layer that is then coupled to the layer referenced in FIGS. 1-5 by numeral 124. Other suitable configurations are also possible.

In some embodiments, the microneedle array 107 can be coupled to the carrier 124 (e.g., if provided by an additional layer that is then coupled to the carrier 124) by a variety of coupling means, including, but not limited to, press-fit or friction-fit engagement, snap-fit engagement, magnets, hook-and-loop fasteners, adhesives, cohesives, clamps, heat sealing, stitches, staples, screws, nails, rivets, brads, crimps, welding (e.g., sonic (e.g., ultrasonic) and/or thermal welding), any thermal bonding technique (e.g., heat and/or pressure applied to one or both of the components to be coupled), other suitable coupling means, or combinations thereof. Alternatively, as shown in FIGS. 1-5, in some embodiments, the carrier 124 and the microneedle array 107 can be integrally formed.

The housing 102, the plunger 104, and/or the microneedle device 106 (e.g., the carrier 124) can be formed of a variety of materials, including but not limited to, thermoset plastics (e.g., acetal resin available under the trade designation DELRIN® DuPont Corporation, Wilmington, Del.; other suitable thermoset plastics, or combinations thereof), thermoformable plastics (e.g., polyethylene, polypropylene, other suitable thermoformable plastics, or combinations thereof), or metals (e.g., stainless steel, aluminum, other suitable metals, or combinations thereof), or combinations thereof.

In some embodiments, the housing 102 can include a first, skin-contacting, surface (or base) 112, which can be generally planar and configured to be positioned toward the skin surface 50. The first surface 112 can be configured to touch the skin surface 50 during application; however, the first surface 112 is generally not configured to remain coupled to the skin 50, and does not include an adhesive. That is, generally, the first surface 112 is a non-adhesive surface. The housing 102 can further include or define a cavity (or chamber, or pocket, or recess, etc.) 114. As shown in FIG. 2, the first surface 112 can define an aperture 115 that opens into the cavity 114. The housing 102, and particularly, the cavity 114 (or a portion thereof) can be configured to house at least a portion of the microneedle device 106 after application of the microneedles 108.

The microneedle device 106 (or the carrier 124) can include a first side 116 comprising the microneedle array 107 and a second side 118 opposite the first side 116. The first side 116 can be oriented toward the first surface 112 of the housing 102 (i.e., positioned to face the skin surface 50). The microneedles 108 can be coupled to, or formed with, the first side 116, such that the microneedle device 106 is (and particularly, the microneedles 108 are) oriented toward the first surface 112 of the housing 102, i.e., positioned to face the skin surface 50.

In some embodiments, as shown in the embodiment illustrated in FIGS. 1-5, the housing 102 can include a first (e.g., upper) portion 120 that comprises or is configured to cooperate with, the plunger 104, and a second (e.g., lower) portion 122 that comprises or is coupled to the connecting member 110 and the microneedle device 106.

As mentioned above, a plurality of connecting members 110 can be employed. By way of example only, two connecting members 110 are employed in the embodiment shown in FIGS. 1-5. The two connecting members 110 of FIGS. 1-5 are each illustrated as being a substantially rectangular, hinged connecting member 110. However, other shapes and configurations of connecting members 110 are possible, such as a continuous ring, and/or connecting members 110 that include a curved section (e.g., an S-shaped curved section) that can in flexure and/or compression of the connecting member 110. In addition, as few as one connecting member 110 and as many as structurally possible or necessary can be employed with applicators of the present disclosure. For simplicity and clarity, one connecting member 110 will be described, but it should be understood that the description of the connecting member 110 can be equally applied to as many connecting members 110 as are employed. However, other configurations are possible, such as the connecting members described and illustrated in US Patent Publication No. 2009/0198189, which is incorporated herein by reference.

The connecting member 110 can be configured to allow the microneedle device 106 to move relative to the housing 102 between:

(i) a first (treatment) position $M_1$ (see FIGS. 1-3 and 5) in which at least a portion of the microneedle device 106 (e.g., the microneedle array 107 or a portion thereof) extends through the aperture 115 and beyond the first surface 112 of the housing 102 (i.e., penetrating the skin 50, if the applicator 100 is positioned adjacent the skin 50, as shown in FIG. 3); and (ii) a second (non-treatment or recessed) position $M_2$ (see FIG. 4) in which the microneedle device 106 is located within the cavity 114 of the housing 102 defined by the housing 102 and recessed relative to the first surface 112 of the housing 102, such that the microneedle device 106 is located away from the skin surface 50 even if the first surface 112 of the housing 102 is in contact with the skin surface 50.

As a result, the connecting member 110 can be configured to toggle the microneedle device 106 between the first position $M_1$ and the second position $M_2$. For example, when a first threshold (e.g., maximum) application force is applied to the first side 116 of the microneedle device 106 (e.g., in a direction substantially perpendicular to the first side 116 of the microneedle device 106), the connecting member 110 will move the microneedle device 106 from the first position $M_1$ to the second position $M_2$. When a second threshold application force is applied to the second side 118 of the microneedle device 106 (e.g., in a direction substantially perpendicular to the second side 118 of the microneedle device 106), the connecting member 110 will move the microneedle device 106 from the second position $M_2$ to the first position $M_1$.

The first and second threshold application forces can be equal in magnitude but opposite in direction. In such embodiments, the first and second threshold application forces can both be referred to as the threshold application force for simplicity, and it can be described that the threshold application force is either applied to the first side 116 of the microneedle device 106 (or in a first direction) or the second side 118 of the microneedle device 106 (or in a second direction that is different, e.g., opposite, from the first direction). However, in some embodiments, the first and second threshold application forces need not be equal in magnitude, e.g., if it is desired that it is easier to move the microneedle device 106 in one direction than the other.

In some embodiments, the threshold application force can be at least 0.8 lbf (3.5 N), in some embodiments, at least 1 lbf (4.4 N), in some embodiments, at least 3 lbf (13.3 N), and in some embodiments, at least 5 lbf (22.2 N). In some embodiments, the threshold application force can be no greater than 10 lbf (44.5 N), in some embodiments, no greater than 5 lbf (22.2 N), and in some embodiments, no greater than 2 lbf (8.9 N).

By controlling the application force that can be applied to the skin 50, the depth of penetration (DOP) can also be controlled. In some embodiments, the average DOP (e.g., across the microneedles 108) can be at least 25 microns, in some embodiments, at least 50 microns, and in some embodiments, at least 100 microns. In some embodiments, the DOP can be no greater than 600 microns, in some embodiments, no greater than 300 microns, in some embodiments, no greater than 250 microns, and in some embodiments, no greater than 50 microns.

Because the microneedles 108 are positioned to puncture the skin 50 when they are extended beyond the first surface 112 (i.e., when the microneedle device 106 is in the first position $M_1$), the first surface 112 is not in contact with the skin 50 when the microneedle device 106 is in the first position $M_1$. As the microneedle device 106 is moved to the second position $M_2$, the first surface 112 can be brought into contact with the skin 50. However, generally, use of the applicator 100 is complete at this stage (i.e., the skin has been treated with the microneedles 108, and the microneedles 108 have been retracted from the skin 50), and the applicator 100 can be removed. The applicator 100 can be removed or lifted away from the skin 50 as soon as the microneedle device 106 is retracted (i.e., moved to the second position $M_2$). As a result, even if the first surface 112 contacts the skin 50 during application, it may only be in contact with the skin 50 for a very brief amount of time, e.g., on the order of 1 or more seconds, or even less than 1 second. That is, the first surface 112 is not used to attach or anchor the applicator 100 to the skin 50 before, during, or after actuation of the applicator 100. Furthermore, the applicator 100 (i.e., the housing 102) is not anchored or held onto the skin 50 at any point, e.g., when the microneedle device 106 is in the first position $M_1$ or the second position $M_2$.

In use, force can be applied to the first side 116 of the microneedle device 106 by the skin 50 when the applicator 100 as a whole is pressed onto skin 50, e.g., in a direction substantially perpendicular to the microneedle device 106. When the first threshold application force is reached, the microneedle device 106 will be moved away from the skin 50, i.e., to the second position $M_2$. By way of example only, the housing 102 can be grasped and pressed toward the skin 50, or in some embodiments, a handle can be coupled to the housing 102, and the handle can be grasped. Either way, it is the housing 102 (or the applicator 100 as a whole) that is pressed toward the skin 50. Unlike some existing systems, the microneedle device 106 is not pressed into the skin 50 by pressing on its second side 118. As a result, in some embodiments, the applicator 100 can be applied manually with one hand.

As the applicator 100 is applied to the skin surface 50, the applicator 100 can be held in an orientation in which the first surface 112 of the housing 102 is generally parallel with the skin surface 50. Such an orientation can be desirable, particularly in embodiments in which the microneedles 108 are oriented generally perpendicularly with respect to the skin surface 50. Parallel alignment of the applicator 100 thus allows for the microneedles 108 to be pressed straight downward into the skin 50, thus minimizing the chance of bending the microneedles 108 and allowing for reproducible penetration of the microneedles 108 of the array 107 to a desired depth (e.g., average depth) in the skin 50. By substantially parallel, it should be understood that the skin 50 is a biological surface and as such has some natural roughness and irregularity. Thus, variations in alignment of the applicator 100 with respect to parallel having a magnitude similar to that of the natural roughness of the skin surface 50 are considered to be substantially parallel.

Figure 5:
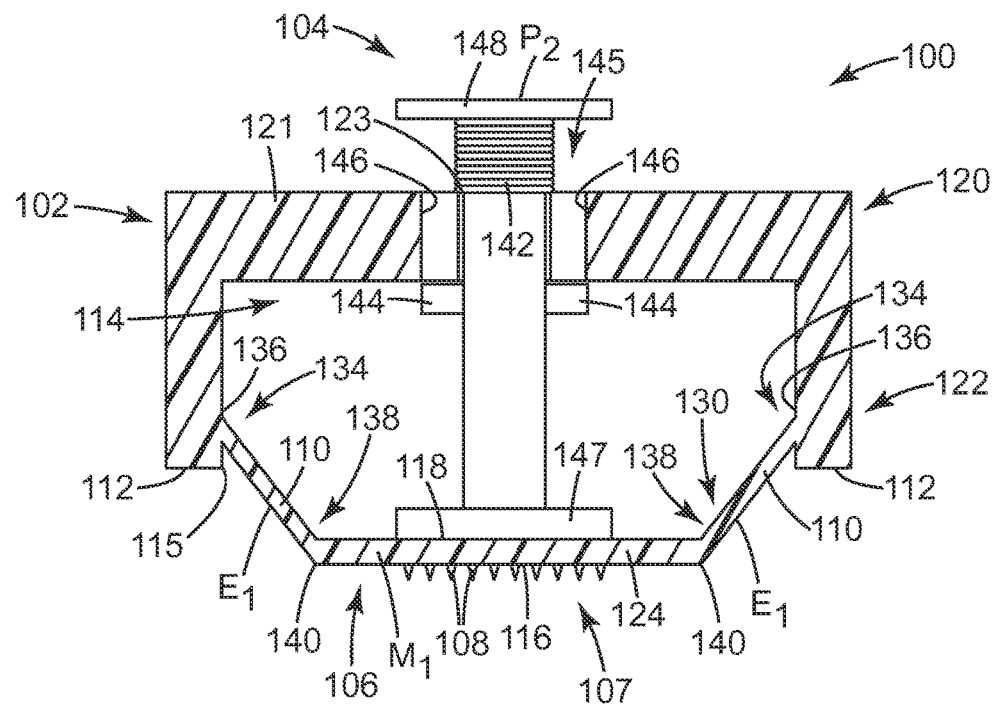
FIG. 5 is a side cross-sectional view of the applicator of FIGS. 1-4, taken along line 3-3 of FIG. 1, the applicator shown with the plunger actuated to return the microneedle device to the first position.

As shown in FIG. 5, in some embodiments, force (e.g., the second threshold application force) can be applied to the second side 118 of the microneedle device 106 by the plunger 104, or another similar structure, to return the microneedle device 106 to the first position $M_1$. In some embodiments, the first portion 120 of the housing 102 can also be open, and returning of the microneedle device 106 to the first position $M_1$ can be accomplished manually. That is, some applicators of the present disclosure do not include the plunger 104, and the plunger 104 is described and illustrated herein by way of example only as a means for returning the microneedle device 106 to its first position $M_1$.

The phrase "directed substantially perpendicularly with respect to the microneedle device" or "in a direction oriented substantially perpendicularly with respect to the microneedle device," or variations thereof, generally refers to a motion that is directed generally perpendicularly or normal to a base or major plane of the microneedle device 106, e.g., normal to a base of the microneedle array 107. For example, in some embodiments, a direction that is "perpendicular with respect to the microneedle device" can be substantially perpendicular to the first side 116 or the second side 118 of the microneedle device 106, and/or to the skin surface 50 to which the microneedle device 106 is being applied. In some embodiments, the microneedle device 106 can include an arcuate first or second side, or an outer surface that has some curvature or undulations. In such embodiments, a direction that is "perpendicular with respect to the microneedle device" would generally refer to a direction that is normal to an outer surface of the microneedle device, e.g., normal to a tangent of such an arcuate surface.

The connecting member 110 can include, or be movable between:
  (i) a first equilibrium position (or state) $E_1$ (see FIGS. 1-3 and 5) in which the microneedle device is in the first position $M_1$; and
  (ii) a second equilibrium position (or state) $E_2$ (see FIG. 4) in which the microneedle device 106 is in the second position $M_2$.

The connecting member 110 can be configured to move from the first equilibrium position $E_1$ to the second equilibrium position $E_2$ (or vice versa) when the threshold application force is met or exceeded, thereby causing the microneedle device 106 to move from the first position $M_1$ to the second position $M_2$, respectively.

The "equilibrium position" or "equilibrium state" of an object is generally used to refer to a position or state in which the potential energy of the object is at a local minimum, and in which the object (e.g., the connecting member 110) can be moved from but which will return to, until a threshold application force is met or exceeded, for example, to move the object to a different equilibrium position (i.e., another local minimum). That is, the object can be moved from and between equilibrium positions when forces less than the threshold application force are applied, but the object will not move to a new equilibrium position until the threshold application force is applied.

A "threshold application force" generally refers to the force required to move an object (e.g., the connecting member 110) to a different equilibrium position. For example, the connecting member 110 can be moved from an equilibrium position (e.g., the first equilibrium position $E_1$) when an application force is applied, but if that application force is less than the threshold application force, the connecting member 110 will return to that same equilibrium position when the application force is removed. When the threshold application force is met or exceeded, however, the connecting member 110 will move to a different equilibrium position (e.g., the second equilibrium position $E_2$). For example, the threshold application force is a force that is sufficient to move the connecting member 110 to a position or configuration that, when the application force is removed, the connecting member 110 will move to a different equilibrium position (e.g., the second equilibrium position $E_2$), rather than returning to the same equilibrium position.

In some embodiments, the equilibrium position can be defined by another component or element of the applicator 100. For example, in some embodiments, the second "true" equilibrium position $E_2$ of the connecting member 110, if it were not restrained by the housing 102, the plunger 104, and/or another element or component of the applicator 100, may be located outside of or beyond (e.g., above) the housing 102, but because the threshold application force has been met or exceeded to move the connecting member toward its "true" second equilibrium position $E_2$, the connecting member 110 (and any object coupled to the connecting member 110, e.g., the microneedle device 106) will remain pressed against the housing 102 or whichever structure is constraining it or providing a stop, in this "pseudo" equilibrium position (or will continue to return to that position), until the threshold application force is applied (e.g., to the microneedle device 106) in an opposite direction to move the connecting member 110 to a different equilibrium position (e.g., back to the first equilibrium position $E_1$).

In some embodiments, the threshold application force can be related to a "transition position" at which the potential energy of the connecting member 110 reaches a local maximum. Transition positions can occur between equilibrium positions. In such cases, the threshold application force can be the force necessary to move the connecting member 110 to a transition position (see, e.g., transition position T in FIG. 3), past which the connecting member 110 will "spring" to a different equilibrium position (e.g., the second equilibrium position $E_2$), thereby pulling the microneedle device 106 with it.

In some embodiments, the connecting member(s) 110 can form a portion of a stored energy device 130. For example, in some embodiments, the connecting member(s) 110, and optionally the carrier 124, can comprise, or function together as, a stored energy device 130. Such a stored energy device 130 can be designed to store a certain amount of potential energy. This potential energy can be converted to kinetic energy when a threshold application force is applied, e.g., in a direction substantially perpendicular to the microneedle device 106, in a direction generally normal to a major plane of the stored energy device 130, and/or in a direction generally orthogonally to the first surface 112 of the housing 102. After the threshold application force is reached, the stored energy device 130 can undergo a bifurcated (i.e., stepwise) motion generally in the direction in which the threshold application force was applied. When the potential energy is converted to kinetic energy, the stored energy device 130, which is coupled to the microneedle device 106, carries or pulls the microneedle device 106 away from the skin surface 50 (i.e., moving the microneedle device 106 to the second position $M_2$).

As a result, the connecting member 110, or the stored energy device 130 comprising the connecting member 110, can be described as having a first equilibrium state or position $E_1$, a second equilibrium state or position $E_2$, and a transition position between the first equilibrium state or position $E_1$, a second equilibrium state or position $E_2$.

Examples of suitable stored energy devices can include, but are not limited to, one or more of bifurcating springs (e.g., Belleville washers, domed springs, etc.), deflected beams, coiled springs, leaf-like springs, hinged springs, propellant canisters, and the like, or combinations thereof. Such springs can be formed of a variety of materials, including, but not limited to, metals, plastics, and combinations thereof. A "bifurcating spring" generally refers to a spring that undergoes a shape change as a result of a predetermined force applied in a direction that is normal (i.e., substantially perpendicularly) to a major plane of the spring.

As shown, in some embodiments, a first portion (e.g., a first end) 134 of the connecting member 110 can be coupled to the housing 102 via a first hinge 136, and a second portion (e.g., a second end) 138 of the connecting member 110 can be coupled to the microneedle device 106 (e.g., the carrier 124) via a second hinge 140. In such embodiments, the connecting member 110 can pivot about the first hinge 136 and the second hinge 140 when moving between the first and second equilibrium positions $E_1$ and $E_2$, and, accordingly, when the microneedle device 106 is moved between its first and second positions $M_1$ and $M_2$. As shown, the connecting member 110 can be coupled to the housing 102 adjacent the aperture 115 or within the cavity 114, such that when the threshold application force is achieved and the connecting member 110 is moved to its second equilibrium position $E_2$, it pulls the microneedle device 106 within the cavity 114. However, other coupling configurations are possible, depending on the type of connecting member that is employed.

As further shown, in some embodiments, the connecting member 110 can be coupled to the housing 102 at a location on, proximal to, or adjacent the first surface (or base) 112. That is, the connecting member 110 can be coupled to the second portion 122 of the housing 102. By coupling the connecting member 110 toward the first surface 112 of the housing 102, the transition point T (or coupling site or pivot point) can also be located lower in the housing 102, which can allow for easier actuation of the applicator 100, can provide a greater distance within the housing 102 for the microneedle device 106 to swing to its second position $M_2$, and can ensure that the connecting member 110 is allowed to move toward its second equilibrium position $E_2$. If the coupling site between the connecting member 110 and the housing 102 is located higher in the housing 102, it can be more difficult to actuate the applicator 100, and to ensure that the connecting member 110 will move to the second equilibrium position $E_2$ and pull the microneedle device 106 to its second position $M_2$. Said another way, if the coupling site between the connecting member 110 and the housing 102 is located higher in the housing 102, the "true" second equilibrium position $E_2$ of the connecting member 110 can be so obstructed that it can be difficult to ensure that the connecting member 110 stays in the second equilibrium position $E_2$, even when the threshold application force has been met.

In some embodiments, the housing 102, the connecting member 110 and the microneedle device 106 (or a portion thereof, such as the carrier 124) can be integrally formed, and the first hinge 136 and the second hinge 140 can be living hinges. In such embodiments, the entire housing 102 need not be integrally formed with the connecting member 110, but rather, the second portion 122 of the housing 102 can be integrally formed with the connecting member 110. The first portion 120 of the housing 102 can be formed separately and/or of a different material and can be coupled to the second portion 122 by any of a variety of coupling means, including, but not limited to, press-fit or friction-fit engagement, snap-fit engagement, magnets, hook-and-loop fasteners, adhesives, cohesives, clamps, heat sealing, stitches, staples, screws, nails, rivets, brads, crimps, welding (e.g., sonic (e.g., ultrasonic) and/or thermal welding), any thermal bonding technique (e.g., heat and/or pressure applied to one or both of the components to be coupled), other suitable coupling means, or combinations thereof.

The connecting member 110 generally includes some flexibility, so as to allow the microneedle device 106 to move between the first position $M_1$ and the second position $M_2$. It should be appreciated that the connecting member 100 is in an extended position in both the first equilibrium position $E_1$ and the second equilibrium position $E_2$, as the distance between the first surface 112 of the housing 102 and the microneedle device 106 is at a maximum. As the microneedle device 106 passes between its first and second positions $M_1$ and $M_2$ and the connecting member 110 passes between the first and second equilibrium positions $E_1$ and $E_2$ (e.g., passes the transition point T—see FIG. 3), however, the distance between the first surface 112 of the housing 102 and the microneedle device 106 is generally reduced.

Generally, the applicator 100 can be configured such that the desired threshold application force can be modified or controlled through a variety of means, including, but not limited to, the shape of the connecting member 110, the rigidity of the connecting member 110, the selection of the hinge type, by adjusting the relative rigidity of the housing 102 and/or the connecting member 110 through a variety of means including material selection or thickness of the material, or combinations thereof. If the applicator 100 (e.g., the first surface 112) and the microneedle device 106 remain substantially parallel to the skin 50, then the distance between the location at which the connecting member 110 is coupled to the housing 102 and the location at which the connecting member 110 is coupled to the microneedle device 106 (e.g., the distance between the first hinge 136 and the second hinge 140) will reach a minimum at the transition point T. If the housing 102 is generally fixed in space (i.e., when pressed onto the skin 50), is relatively rigid and inflexible, and the microneedle device 106 (e.g., the carrier 124) is relatively rigid and inflexible, then the connecting member 110 will be either compressed or flexed to accommodate this reduction in distance as the microneedle device 106 is moved between its first and second positions $M_1$ and $M_2$. In some embodiments, as shown in FIGS. 1-5, the connecting member 110 can be made of a thin, relatively flexible material that may bow or arch as the microneedle device 106 moves between its first and second positions $M_1$ and $M_2$ and as the connecting member 110 moves between the first and second equilibrium positions $E_1$ and $E_2$.

When the microneedle device 106 is in the first position $M_1$, the distance D (see FIG. 3) between the first surface 112 of the housing 102 and the microneedle device 106 (e.g., illustrated as the distance between the first side 116 of the microneedle device 106 and the first surface 112) is at least as much as, and is generally greater than the distance the skin 50 is deflected when the threshold application force is applied to the skin 50. Similar to coupling the connecting member 110 toward the first surface 112 of the housing 102, controlling the distance D to be greater than the skin deflection that occurs in achieving the threshold application force, can allow for easier actuation of the applicator 100, and can ensure that the threshold application force is achieved before, or as, the first surface 112 contacts the skin 50. If the distance D were shorter, it may be more difficult to achieve the threshold application force before, or as, the first surface 112 contacts the skin 50. If the threshold application force is not met before the first surface 112 contacts the skin 50, enough force would have been applied to begin moving the connecting member 110 away from its first equilibrium position $E_1$, but not enough force to move it to its second equilibrium position $E_2$ and retract the microneedle device 106 from the skin 50.

In some embodiments, the distance D can be at least 0.5 mm, in some embodiments, at least 1 mm, in some embodiments, at least 2 mm, and in some embodiments, at least 3 mm. In some embodiments, the distance D can be no greater than 25 mm, in some embodiments, no greater than 20 mm, in some embodiments, no greater than 15 mm, in some embodiments, no greater than 13 mm, in some embodiments, no greater than 10 mm, and in some embodiments, no greater than 5 mm.

The plunger 104 can be moved with respect to the housing 102 (e.g., the first portion 120 of the housing 102) between a first (return) position $P_1$ (see FIGS. 1-4) and a second (actuated) position $P_2$ (see FIG. 5) to move the microneedle device 106 to its first position $M_1$ (e.g., from the second position $M_2$, i.e., to return the microneedle device 106 to the first position $M_1$ to allow the applicator 100 and/or the microneedle device 106 to be reused, e.g., with the same or a different microneedle array 107). The plunger 104 is illustrated as being long enough to fully return the microneedle device 106 to its first position $M_1$, however, it should be understood that the plunger 104 need not have the length shown. Rather, the plunger 104 (if employed) can have a different configuration as long as the plunger 104 is configured to apply the threshold application force and/or move the microneedle device 106 past the transition point T, after which the connecting member 110 will pull the microneedle device 106 to its first position $M_1$ (and return the connecting member 110 to its first equilibrium position $E_1$).

The microneedle device 106 can be configured to move from its first position $M_1$ to its second position $M_2$ in a first direction, and the plunger 104 can be configured to move from its first position $P_1$ to its second position $P_2$ in a second direction oriented substantially perpendicularly with respect to the microneedle device 106. The second direction (as described above) can be different from the first direction, e.g., the second direction can be opposite the first direction.

As a result, as shown in FIG. 5, the plunger 104 can be used to apply the threshold application force to the second side 118 of the microneedle device 106 (e.g., the second threshold application force) to cause the connecting member 110 to move to its first equilibrium position $E_1$ and to move the microneedle device 106 to its first position $M_1$.

By way of example only, the plunger 104 is illustrated as being biased toward its first position $P_1$ by a spring 142. By way of further example, the plunger 104 is illustrated as being able to be locked in its first position $P_1$ by a twist-lock mechanism 145. The housing 102 (e.g., the first portion 120 of the housing 102) can include an upper wall 121 and an aperture (or bore) 123 formed therein, the aperture 123 being dimensioned to receive the plunger 140, or at least a shaft 143 thereof.

The locking mechanism 145 can include one or more (two are illustrated by way of example) projections 144 that extend outwardly (e.g., radially-outwardly) from a periphery or outer surface (e.g., from an outer circumferential surface of the shaft 143) of the plunger 304.

The plunger 104 and/or the housing 102 can be configured such that the plunger 104 and/or the housing 102 can be rotated (or twisted) relative to one another. For example, the plunger 104 can be rotated in the aperture 123 formed in the housing 102. As such, the housing 102 can be shaped and configured to allow the one or more projections 144 to move relative to the housing 102. As shown, in some embodiments, the aperture 123 in the upper wall 121 of the housing 102 can include or one or more corresponding recesses (or notches or slots) 146.

The recesses 146 can be dimensioned to allow the projections 144 to pass therethrough to move the plunger 104 relative to the housing 102 when the projections 144 are properly aligned with the recesses 146. When it is desired to lock the plunger 104 in its first position $P_1$, the plunger 104 and/or the housing 102 can be rotated (or twisted) such that the projections 144 not aligned with the recesses 146 (see FIG. 1).

When the plunger 104 is in its first position $P_1$, the plunger 104 (e.g., base or end 147 thereof) can act as a backstop for the microneedle device 106 (e.g., when in its second position $M_2$). When it is desired to move (e.g., return) the microneedle device 106 to its first position $M_1$ (and to return the connecting member 110 to its first equilibrium position $E_1$), the plunger 104 can be rotated to align the projections 144 with the recesses 146 such that the projections 144 can pass through the recesses 146, and the plunger 104 can be depressed downwardly, e.g., against the bias of the spring 142. The shaft 143 of the plunger 104 will then move downwardly in the aperture 123, relative to the housing 102, moving the plunger 104 from its first position $P_1$ to its second position $P_2$, thereby pressing against the microneedle device 106. When the plunger 104 has applied the threshold application force to the second side 118 of the microneedle device 106 (e.g., the second threshold application force), the connecting member 110 will be moved to its first equilibrium position $E_1$, causing the microneedle device 106 to move to its first position $M_1$.

Two projections 144 and recesses 146 that are located 180 degrees apart about the periphery of the plunger 104 are shown by way of example only. However, it should be understood that such a twist-lock engaging locking mechanism 145 can include as few as one projection 144 and corresponding recess 146 or as many as desired.

FIGS. 1, 3 and 4 show the plunger 104 rotated 90 degrees relative to the housing 102 and relative to its angular position in FIG. 5, such that the first position $P_1$ of the plunger 104 and second position $P_2$ of the plunger 104 are separated 90 degrees from one another. However, it should be understood that the applicator 100 can be configured to be rotated less than 90 degrees or greater than 90 degrees, and that the illustrated 90-degree configuration is shown by way of example only.

In some embodiments, a cap 148 of the plunger 104 can include one or more upwardly-extending fins or projections to facilitate grasping the plunger 104 for twisting. In embodiments employing the spring 142, the spring 142 can be located between a cap 148 and the one or more projections 144.

The plunger 104 is illustrated as being upwardly biased (i.e., toward its first position $P_1$) by way of example only; however, it should be understood that the plunger 104 can instead be biased downwardly (e.g., by locating the spring 142 between the upper wall 121 of the housing 102 and the base 147 of the plunger 104), or need not be biased at all. In embodiments in which the plunger 104 is biased downwardly, it can still be held or locked in the upward, first position $P_1$, and can be "fired" when desired to its second position $P_2$.

In addition, the twist-lock mechanism 145 is shown by way of example only, and it should be understood that a variety of other mechanisms can be employed to control the movement of the plunger 104.

As mentioned above, in some embodiments, active ingredients or agents (e.g., drugs) can be delivered via the microneedles 108 (e.g., via solid microneedles, as described below). Examples of pharmaceutically active agents (also referred to as "drugs") that can be incorporated into the applicators of the present disclosure are those capable of local or systemic effect when administered to the skin. Some examples include buprenorphine, clonidine, diclofenac, estradiol, granisetron, isosorbide dinitrate, levonorgestrel, lidocaine, methylphenidate, nicotine, nitroglycerine, oxybutynin, rivastigmine, rotigotine, scopolamine, selegiline, testosterone, tulobuterol, and fentanyl, which are commercially available in the form of transdermal devices. Other examples include antiinflammatory drugs, both steroidal (e.g., hydrocortisone, prednisolone, triamcinolone) and nonsteroidal (e.g., naproxen, piroxicam); bacteriostatic agents (e.g., chlorhexidine, hexylresorcinol); antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin); antiprotazoals (e.g., metronidazole); antifungals (e.g., nystatin); coronary vasodilators; calcium channel blockers (e.g., nifedipine, diltiazem); bronchodilators (e.g., theophylline, pirbuterol, salmeterol, isoproterenol); enzyme inhibitors such as collagenase inhibitors, protease inhibitors, acetylcholinesterase inhibitors (e.g., donepezil), elastase inhibitors, lipoxygenase inhibitors (e.g., A64077), and angiotensin converting enzyme inhibitors (e.g., captopril, lisinopril); other antihypertensives (e.g., propranolol); leukotriene antagonists (e.g., ICI204,219); anti-ulceratives such as H2 antagonists; steroidal hormones (e.g., progesterone); antivirals and/or immunomodulators (e.g., 1-isobutyl-1H-imidazo[4,5-c]quinolin-4-amine, 1-(2-hydroxy-2-methylpropyl)-1H-imidazo[4,5-c]quinolin-4-amine, N-[4-(4-amino-2-ethyl-1H-imidazo[4,5-c]quinolin-1-yl)butyl] methanesulfonamide, and acyclovir); local anesthetics (e.g., benzocaine, propofol, tetracaine, prilocaine); cardiotonics (e.g., digitalis, digoxin); antitussives (e.g., codeine, dextromethorphan); antihistamines (e.g., diphenhydramine, chlorpheniramine, terfenadine); narcotic analgesics (e.g., morphine, fentanyl citrate, sufentanil, hydromorphone hydrochloride); peptide hormones (e.g., human or animal growth hormones, LHRH, parathyroid hormones); cardioactive products such as atriopeptides; antidiabetic agents (e.g., insulin, exanatide); enzymes (e.g., anti-plaque enzymes, lysozyme, dextranase); antinauseants; anticonvulsants (e.g., carbamazine); immunosuppressives (e.g., cyclosporine); psychotherapeutics (e.g., diazepam); sedatives (e.g., phenobarbital); anticoagulants (e.g., heparin, enoxaparin sodium); analgesics (e.g., acetaminophen); antimigraine agents (e.g., ergotamine, melatonin, sumatriptan, zolmitriptan); antiarrhythmic agents (e.g., flecainide); antiemetics (e.g., metaclopromide, ondansetron, granisetron hydrochloride); anticancer agents (e.g., methotrexate); neurologic agents such as anxiolytic drugs; hemostatics; antiobesity agents; dopamine agonists (e.g., apomorphine); GnRH agonists (e.g., leuprolide, goserelin, nafarelin); fertility hormones (e.g., hCG, hMG, urofollitropin); interferons (e.g., interferon-alpha, interferon-beta, interferon-gamma, pegylated interferon-alpha); and the like, as well as pharmaceutically acceptable salts and esters thereof. The amount of drug that constitutes a therapeutically effective amount can be readily determined by those skilled in the art with due consideration of the particular drug, the particular carrier, and the desired therapeutic effect.

In some embodiments, peptide therapeutic agents (natural, synthetic, or recombinant) can be delivered via the microneedles 108 (e.g., via solid microneedles). Examples of peptide therapeutic agents that can be incorporated into the applicators of the present disclosure include parathyroid hormone (PTH), parathyroid hormone related protein (PTHrP), calcitonin, lysozyme, insulin, insulinotropic analogs, glatiramer acetate, goserelin acetate, somatostatin, octreotide, leuprolide, vasopressin, desmopressin, thymosin alpha-1, atrial natriuretic peptide (ANP), endorphin, vascular endothelial growth factor (VEGF), fibroblast-growth factor (FGF), erythropoietin (EPO), bone morphogenetic proteins (BMPs), epidermal growth factor (EFG), granulocyte colony-stimulating factor (G-CSF), granulocyte macrophage colony stimulating factor (GM-CSF), insulin-like growth factor (IGF), platelet-derived growth factor (PDGF), growth hormone release hormone (GHRH), dornase alfa, tissue plasminogen activator (tPA), urokinase, ANP clearance inhibitors, lutenizing hormone releasing hormone (LHRH), melanocyte stimulating hormones (alpha & beta MSH), pituitary hormones (hGH), adrenocorticotropic hormone (ACTH), human chorionic gonadotropin (hCG), streptokinase, interleukins (e.g. IL-2, IL-4, IL-10, IL-12, IL-15, IL-18), protein C, protein S, angiotensin, angiogenin, endothelins, pentigetide, brain natriuretic peptide (BNP), neuropeptide Y, islet amyloid polypeptide (IAPP), vasoactive intestinal peptide (VIP), hirudin, glucagon, oxytocin, and derivatives of any of the foregoing peptide therapeutic agents.

In some embodiments, drugs that are of a large molecular weight may be delivered transdermally. Increasing molecular weight of a drug typically can cause a decrease in unassisted transdermal delivery. Examples of such large molecules include proteins, peptides, nucleotide sequences, monoclonal antibodies, vaccines, polysaccharides, such as heparin, and antibiotics, such as ceftriaxone. Examples of suitable vaccines include therapeutic cancer vaccines, anthrax vaccine, flu vaccine, Lyme disease vaccine, rabies vaccine, measles vaccine, mumps vaccine, chicken pox vaccine, small pox vaccine, hepatitis vaccine, hepatitis A vaccine, hepatitis B vaccine, hepatitis C vaccine, pertussis vaccine, rubella vaccine, diphtheria vaccine, encephalitis vaccine, Japanese encephalitis vaccine, respiratory syncytial virus vaccine, yellow fever vaccine, recombinant protein vaccine, DNA vaccines, polio vaccine, therapeutic cancer vaccine, herpes vaccine, human papilloma virus vaccine, pneumococcal vaccine, meningitis vaccine, whooping cough vaccine, tetanus vaccine, typhoid fever vaccine, cholera vaccine, tuberculosis vaccine, severe acute respiratory syndrome (SARS) vaccine, HSV-1 vaccine, HSV-2 vaccine, HIV vaccine and combinations thereof. The term "vaccine" thus includes, without limitation, antigens in the forms of proteins, polysaccharides, oligosaccharides, or weakened or killed viruses. Additional examples of suitable vaccines and vaccine adjuvants are described in U.S. Publication No. 2004/0049150 (Dalton et al.), the disclosure of which is hereby incorporated by reference.

In another embodiment, small-molecule drugs that are otherwise difficult or impossible to deliver by passive transdermal delivery may be used. Examples of such molecules include salt forms; ionic molecules, such as bisphosphonates, including sodium alendronate or pamedronate; and molecules with physicochemical properties that are not conducive to passive transdermal delivery.

In some embodiments, the microneedles 108 can be solid. In such embodiments, if an active agent is to be delivered to the skin, the active agent can be applied to the microneedles 108 by a variety of techniques, including, but not limited to painting (e.g., brushing), coating, dipping, or the like, or combinations thereof.

Microneedle arrays useful for practicing the present disclosure can have a variety of configurations and features, such as those described in the following patents and patent applications, the disclosures of which are incorporated herein by reference. One embodiment for the microneedle arrays 107 includes the structures disclosed in U.S. Patent Application Publication No. 2005/0261631 (Clarke et al.), which describes microneedles having a truncated tapered shape and a controlled aspect ratio. Another embodiment for the microneedle arrays 107 includes the structures disclosed in U.S. Pat. No. 6,091,975 (Daddona et al.), which describes blade-like microprotrusions for piercing the skin. Still another embodiment for the microneedle arrays 107 includes the structures disclosed in U.S. Pat. No. 6,312,612 (Sherman et al.), which describes tapered structures having a hollow central channel. Yet still another embodiment for the microneedle arrays 107 includes the structures disclosed in U.S. Pat. No. 6,379,324 (Garstein et al.), which describes hollow microneedles having at least one longitudinal blade at the top surface of the tip of the microneedle. A further embodiment for the microneedle arrays 107 includes the structures disclosed in U.S. Patent Application Publication Nos. US2012/0123387 (Gonzalez et al.) and US2011/0213335 (Burton et al.), which both describe hollow microneedles. A still further embodiment for the microneedle arrays 107 includes the structures disclosed in U.S. Pat. No. 6,558,361 (Yeshurun) and U.S. Pat. No. 7,648,484 (Yeshurun et al.), which both describe hollow microneedle arrays and methods of manufacturing thereof.

Various embodiments of microneedles that can be employed in the microneedle arrays of the present disclosure are described in PCT Publication No. WO 2012/074576 (Duan et al.), which describes liquid crystalline polymer (LCP) microneedles; and PCT Publication No. WO 2012/122162 (Zhang et al.), which describes a variety of different types and compositions of microneedles that can be employed in the microneedles of the present disclosure.

In some embodiments, the microneedle material can be (or include) silicon, glass, or a metal such as stainless steel, titanium, or nickel titanium alloy. In some embodiments, the microneedle material can be (or include) a polymeric material, preferably a medical grade polymeric material. Exemplary types of medical grade polymeric materials include polycarbonate, liquid crystalline polymer (LCP), polyether ether ketone (PEEK), cyclic olefin copolymer (COC), polybutylene terephthalate (PBT). Preferred types of medical grade polymeric materials include polycarbonate and LCP.

In some embodiments, the microneedle material can be (or include) a biodegradable polymeric material, preferably a medical grade biodegradable polymeric material. Exemplary types of medical grade biodegradable materials include polylactic acid (PLA), polyglycolic acid (PGA), PGA and PLA copolymer, polyester-amide polymer (PEA).

A microneedle or the plurality of microneedles in a microneedle array useful for practicing the present disclosure can have a variety of shapes that are capable of piercing the stratum corneum. In some embodiments, one or more of the plurality of microneedles can have a square pyramidal shape, triangular pyramidal shape, stepped pyramidal shape, conical shape, microblade shape, or the shape of a hypodermic needle. In some embodiments, one or more of the plurality of microneedles can have a square pyramidal shape. In some embodiments, one or more of the plurality of microneedles can have a triangular pyramidal shape. In some embodiments, one or more of the plurality of microneedles can have a stepped pyramidal shape. In some embodiments, one or more of the plurality of microneedles can have a conical shape. In some embodiments, one or more of the plurality of microneedles can have a microblade shape. In some embodiments, one or more of the plurality of microneedles can have the shape of a hypodermic needle. The shape can be symmetric or asymmetric. The shape can be truncated (for example, the plurality of microneedles can have a truncated pyramid shape or truncated cone shape). In a preferred embodiment, the plurality of microneedles in a microneedle array each have a square pyramidal shape.

In some embodiments, the plurality of microneedles in a microneedle array are solid microneedles (that is, the microneedles are solid throughout). In some embodiments, the plurality of solid microneedles in a solid microneedle array can have a square pyramidal shape, triangular pyramidal shape, stepped pyramidal shape, conical shape, or microblade shape. In a preferred embodiment, the plurality of solid microneedles in a solid microneedle array each have a square pyramidal shape.

In some embodiments, the plurality of microneedles in a microneedle array are hollow microneedles (that is, the microneedles contain a hollow bore through the microneedle). The hollow bore can be from the base of the microneedle to the tip of the microneedle or the bore can be from the base of the microneedle to a position offset from the tip of the microneedle. In some embodiments, one or more of the plurality of hollow microneedles in a hollow microneedle array can have a conical shape, cylindrical shape, square pyramidal shape, triangular pyramidal shape, or the shape of a hypodermic needle.

In some embodiments, one or more of the plurality of hollow microneedles in a hollow microneedle array can have a conical shape. In some embodiments, one or more of the plurality of hollow microneedles in a hollow microneedle array can have a cylindrical shape. In some embodiments, one or more of the plurality of hollow microneedles in a hollow microneedle array can have a square pyramidal shape. In some embodiments, one or more of the plurality of hollow microneedles in a hollow microneedle array can have a triangular pyramidal shape. In some embodiments, one or more of the plurality of hollow microneedles in a hollow microneedle array can have the shape of a hypodermic needle. In a preferred embodiment, the plurality of hollow microneedles in a hollow microneedle array each have the shape of a conventional hypodermic needle.

Figure 6:
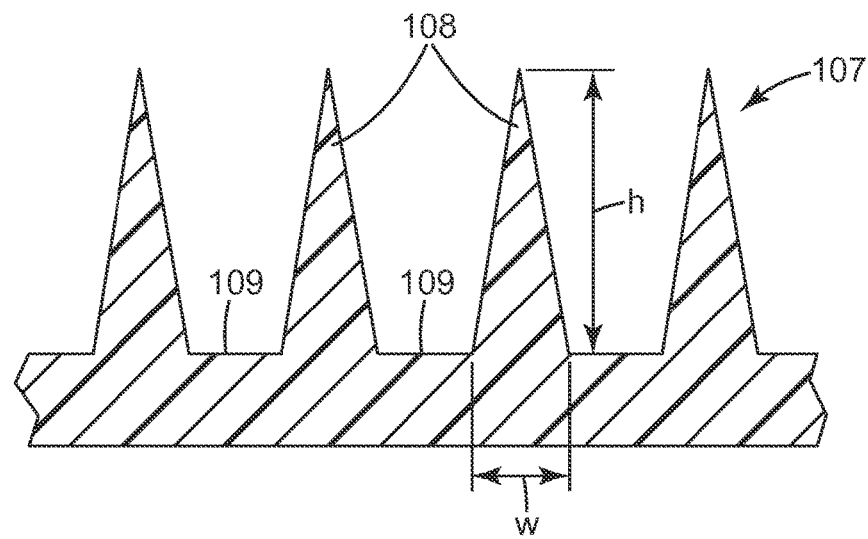
FIG. 6 is a close-up side cross-sectional view of the microneedle array of FIGS. 2-5 (shown with the microneedles pointing upwardly).

FIG. 6 shows a portion of the microneedle array 107 that includes four microneedles 108 (of which two are referenced in FIG. 6) positioned on a microneedle substrate 109 (e.g., which can be the carrier 124 or another layer coupled to the carrier 124). Each microneedle 108 has a height h, which is the length from the tip of the microneedle 108 to the microneedle base at substrate 109. Either the height of a single microneedle or the average height of all microneedles on the microneedle array can be referred to as the height of the microneedle, h. In some embodiments, each of the plurality of microneedles (or the average of all of the plurality of microneedles) has a height of about 100 to about 3000 micrometers, in some embodiments, about 100 to about 1500 micrometers, in some embodiments, about 100 to about 1200 micrometers, and, in some embodiments, about 100 to about 1000 micrometers.

In some embodiments, each of the plurality of microneedles (or the average of all of the plurality of microneedles) has a height of about 200 to about 1200 micrometers, about 200 to about 1000 micrometers, about 200 to about 750 micrometers, or about 200 to about 600 micrometers.

In some embodiments, each of the plurality of microneedles (or the average of all of the plurality of microneedles) has a height of about 250 to about 1500 micrometers, about 500 to about 1000 micrometers, or about 500 to about 750 micrometers.

In some embodiments, each of the plurality of microneedles (or the average of all of the plurality of microneedles) has a height of about 800 to about 1400 micrometers.

In some embodiments, each of the plurality of microneedles (or the average of all of the plurality of microneedles) has a height of about 500.

In some embodiments, each of the plurality of microneedles (or the average of all of the plurality of microneedles) has a height of less than about 3000 micrometers. In other embodiments, each of the plurality of microneedles (or the average of all of the plurality of microneedles) has a height of less than about 1500 micrometers. In still other embodiments, each of the plurality of microneedles (or the average of all of the plurality of microneedles) has a height of less than about 1200 micrometers. In yet still other embodiments, each of the plurality of microneedles (or the average of all of the plurality of microneedles) has a height of less than about 1000 micrometers. In further embodiments, each of the plurality of microneedles (or the average of all of the plurality of microneedles) has a height of less than about 750 micrometers. In still further embodiments, each of the plurality of microneedles (or the average of all of the plurality of microneedles) has a height of less than about 600 micrometers.

In some embodiments, each of the plurality of microneedles (or the average of all of the plurality of microneedles) has a height of at least about 100 micrometers. In other embodiments, each of the plurality of microneedles (or the average of all of the plurality of microneedles) has a height of at least about 200 micrometers. In still other embodiments, each of the plurality of microneedles (or the average of all of the plurality of microneedles) has a height of at least about 250 micrometers. In further embodiments, each of the plurality of microneedles (or the average of all of the plurality of microneedles) has a height of at least about 500 micrometers. In still further embodiments, each of the plurality of microneedles (or the average of all of the plurality of microneedles) has a height of at least about 800 micrometers.

A single microneedle or the plurality of microneedles in a microneedle array can also be characterized by their aspect ratio. The aspect ratio of a microneedle is the ratio of the height of the microneedle, h to the width (at the base of the microneedle), w (as shown in FIG. 12). The aspect ratio can be presented as h:w. In some embodiments, each of the plurality of microneedles (or the average of all the plurality of microneedles) has (have) an aspect ratio in the range of 2:1 to 5:1. In some of these embodiments, each of the plurality of microneedles (or the average of all of the plurality of microneedles) has (have) an aspect ratio of at least 3:1.

In some embodiments, the array of microneedles contains about 100 to about 1500 microneedles per cm$^2$ of the array of microneedles.

In some embodiments, the array of microneedles contains about 200 to about 500 microneedles per cm$^2$ of the array of microneedles.

In some embodiments, the array of microneedles contains about 300 to about 400 microneedles per cm$^2$ of the array of microneedles.

In some embodiments, the array of microneedles contains about 3 to about 30 microneedles per cm$^2$ of the array of microneedles.

In some embodiments, the array of microneedles contains about 3 to about 20 microneedles per cm$^2$ of the array of microneedles.

In some embodiments, the array of microneedles contains about 10 to about 20 microneedles per cm$^2$ of the array of microneedles.

In some embodiments, each of the plurality of microneedles (or the average of all of the plurality of microneedles) in a microneedle array can penetrate into the skin to a depth of about 50 to about 1500 micrometers, about 50 to about 400 micrometers, or about 50 to about 250 micrometers.

In some embodiments, each of the plurality of microneedles (or the average of all of the plurality of microneedles) in a microneedle array can penetrate into the skin to a depth of about 100 to about 400 micrometers, or about 100 to about 300 micrometers.

In some embodiments, each of the plurality of microneedles (or the average of all of the plurality of microneedles) in a microneedle array can penetrate into the skin to a depth of about 150 to about 1500 micrometers, or about 800 to about 1500 micrometers.

In some embodiments, each of the plurality of microneedles (or the average of all of the plurality of microneedles) in a microneedle array can penetrate into the skin to a depth of about 400 to about 800 micrometers.

The microneedles 108 can be arranged in any desired pattern or distributed over the microneedle substrate 109 randomly. As shown in FIG. 1, in some embodiments, the microneedles 108 can be arranged in uniformly spaced rows. When arranged in rows, the rows can be arranged so that the microneedles 108 are aligned or offset. In some embodiments (not shown), the microneedles 108 can be arranged in a polygonal pattern such as a triangle, square, rectangle, pentagon, hexagon, heptagon, octagon, or trapezoid. In other embodiments (not shown), the microneedles 108 can be arranged in a circular or oval pattern.

In some embodiments, the surface area of the substrate 109 (which can be the carrier 124 or another layer coupled thereto) covered with microneedles 108 is about 0.1 cm$^2$ to about 20 cm$^2$. In some of these embodiments, the surface area of the substrate 109 covered with microneedles 108 is about 0.5 cm$^2$ to about 5 cm$^2$. In some other of these embodiments, the surface area of the substrate 109 covered with microneedles 108 is about 1 cm$^2$ to about 3 cm$^2$. In still other of these embodiments, the surface area of the substrate 109 covered with microneedles 108 is about 1 cm$^2$ to about 2 cm$^2$.

In some embodiments, the microneedles of the present disclosure can be disposed over substantially the entire surface of the array. In other embodiments (e.g., as shown in FIG. 1), a portion of the substrate 109 (e.g., the carrier 124) may not be provided with microneedles (that is, a portion of the substrate is non-structured). In some of these embodiments, the non-structured surface has an area of more than about 1 percent and less than about 75 percent of the total area of the device surface that faces the skin surface. In another of these embodiments, the non-structured surface has an area of more than about 0.65 cm$^2$ (0.10 square inch) to less than about 6.5 cm$^2$ (1 square inch).

In some embodiments of microneedle arrays, the average spacing between adjacent microneedles (as measured from microneedle tip to microneedle tip) is between about 200 micrometers and about 2000 micrometers. In other embodiments of microneedle arrays, the average spacing between adjacent microneedles is between about 200 micrometers and about 600 micrometers. In still other embodiments of microneedle arrays, the average spacing between adjacent microneedles is between about 200 micrometers and about 300 micrometers. In yet still other embodiments of microneedle arrays, the average spacing between adjacent microneedles is between about 500 micrometers and about 600 micrometers.

In some embodiments of microneedle arrays, the average spacing between adjacent microneedles (as measured from microneedle tip to microneedle tip) is greater than about 200 micrometers. In other embodiments of microneedle arrays, the average spacing between adjacent microneedles is greater than about 500 micrometers.

In some embodiments of microneedle arrays, the average spacing between adjacent microneedles is less than about 2000 micrometers. In other embodiments of microneedle arrays, the average spacing between adjacent microneedles is less than about 1000 micrometers. In still other embodiments of microneedle arrays, the average spacing between adjacent microneedles is less than about 600 micrometers. In yet still other embodiments of microneedle arrays, the average spacing between adjacent microneedles is less than about 300 micrometers.

The microneedle arrays can be manufactured in any suitable way such as by injection molding, compression molding, metal injection molding, stamping, photolithography, or extrusion.

The following embodiments are intended to be illustrative of the present disclosure and not limiting.

EMBODIMENTS

Embodiment 1 is an applicator for applying a microneedle device to a skin surface, the applicator comprising:
    a microneedle device having a first side comprising a microneedle array and a second side opposite the first side, the first side configured to be positioned toward the skin surface;

a housing having a first surface configured to be positioned toward the skin surface; and a connecting member positioned to couple the microneedle device to the housing and configured to allow the microneedle device to move relative to the housing between a first position in which at least a portion of the microneedle device extends beyond the first surface of the housing, and a second position in which the microneedle device is recessed within the housing, such that the microneedle device does not extend beyond the first surface of the housing, wherein the connecting member is configured to move the microneedle device to the second position when a threshold application force is applied to the first side of the microneedle device in a direction substantially perpendicular with respect to the microneedle device, and wherein the first surface of the housing is not in contact with the skin surface when the microneedle device is in the first position.

Embodiment 2 is the applicator of embodiment 1, wherein the applicator is configured to be pressed in a direction substantially perpendicular to the microneedle device when the microneedle device is in the first position to press the microneedle device into the skin surface until the threshold application force is reached and the microneedle device is moved from the first position to the second position.

Embodiment 3 is a method of applying a microneedle device to a skin surface, the method comprising:

providing the applicator of embodiment 1;

pressing the applicator in a direction substantially perpendicular to the microneedle device into the skin surface when the microneedle device is in the first position until the threshold application force is met or exceeded; and moving the microneedle device to the second position in response to meeting or exceeding the threshold application force.

Embodiment 4 is the applicator of embodiment 1 or 2 or the method of embodiment 3, wherein the connecting member has a first equilibrium position in which the microneedle device is in the first position, and a second equilibrium position in which the microneedle device is in the second position; and wherein the connecting member is configured to move to the second equilibrium position when the threshold application force is met or exceeded.

Embodiment 5 is the applicator of any of embodiments 1, 2 and 4 or the method of embodiment 3 or 4, wherein the connecting member is coupled to the housing via a first hinge, and wherein the connecting member is coupled to the microneedle device via a second hinge.

Embodiment 6 is the applicator of any of embodiments 1, 2, 4 and 5 or the method of any of embodiments 3-5, wherein a first portion of the connecting member is coupled to the housing via a first hinge, and a second portion of the connecting member is coupled to the microneedle device via a second hinge.

Embodiment 7 is the applicator or method of embodiment 5 or embodiment 6, wherein the connecting member pivots about the first hinge and the second hinge when the microneedle device is moved between the first position and the second position.

Embodiment 8 is the applicator or method of any of embodiments 5-7, wherein the first hinge and the second hinge are living hinges.

Embodiment 9 is the applicator of any of embodiments 1, 2, 4 and 5-8 or the method of any of embodiments 3-8, wherein the connecting member comprises a bifurcating spring.

Embodiment 10 is the applicator of any of embodiments 1, 2, 4 and 5-9 or the method of any of embodiments 3-9, wherein the threshold application force is a first threshold application force, and wherein the connecting member is configured to move the microneedle device to the first position when a second threshold application force is applied to the second side of the microneedle device in a direction oriented substantially perpendicularly with respect to the microneedle device.

Embodiment 11 is the applicator of any of embodiments 1, 2, 4 and 5-10 or the method of any of embodiments 3-10, wherein the second threshold application force is equal and opposite to the first threshold application force.

Embodiment 12 is the applicator of any of embodiments 1, 2, 4 and 5-11 or the method of any of embodiments 3-11, wherein the connecting member is further configured to move the microneedle device to the first position when the threshold application force is applied to the second side of the microneedle device in a direction oriented substantially perpendicularly with respect to the microneedle device.

Embodiment 13 is the applicator of any of embodiments 1, 2, 4 and 5-12, further comprising a plunger movable with respect to the housing between a first position and a second position to move the microneedle device to the first position.

Embodiment 14 is the applicator of embodiment 13, wherein the microneedle device is configured to move from its first position to its second position in a first direction, and wherein the plunger is configured to move from its first position to its second position in a second direction that is opposite the first direction and oriented substantially perpendicularly with respect to the microneedle device.

Embodiment 15 is the method of any of embodiments 3-12, further comprising moving the microneedle device from the second position to the first position.

Embodiment 16 is the method of any of embodiments 3-12 and 15, further comprising returning the microneedle device to the first position.

Embodiment 17 is the method of embodiment 16, wherein the applicator further comprises a plunger movable with respect to the housing between a first position and a second position, and wherein returning the microneedle device to the first position includes moving the plunger from its first position to its second position.

Embodiment 18 is the method of embodiment 16 or 17, wherein moving the microneedle device from the first position to the second position includes moving the microneedle device in a first direction oriented substantially perpendicularly with respect to the microneedle device, and wherein returning the microneedle device to the first position includes moving the microneedle device in a second direction that is opposite the first direction.

Embodiment 19 is the method of any of embodiments 16-18, wherein the threshold application force is a first threshold application force, and wherein returning the microneedle device to the first position includes applying a second threshold application force to the second side of the microneedle device.

Embodiment 20 is the method of embodiment 19, wherein the second threshold application force is equal and opposite to the first threshold application force.

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure.

All references and publications cited herein are expressly incorporated herein by reference in their entirety into this disclosure.

Various features and aspects of the present disclosure are set forth in the following claims.

What is claimed is:

1. An applicator for applying a microneedle device to a skin surface, the applicator comprising:
   a microneedle device having a first side comprising a microneedle array and a second side opposite the first side, the first side configured to be positioned toward the skin surface;
   a housing having a first surface configured to be positioned toward the skin surface; and
   a connecting member positioned to couple the microneedle device to the housing and configured to allow the microneedle device to move relative to the housing between
      a first position in which at least a portion of the microneedle device extends beyond the first surface of the housing, and
      a second position in which the microneedle device is recessed within the housing, such that the microneedle device does not extend beyond the first surface of the housing,
   wherein the connecting member is configured to move the microneedle device to the second position when a threshold application force is applied to the first side of the microneedle device in a direction substantially perpendicular with respect to the microneedle device, and wherein the first surface of the housing is not in contact with the skin surface when the microneedle device is in the first position.

2. The applicator of claim 1, wherein the applicator is configured to be pressed in a direction substantially perpendicular to the microneedle device when the microneedle device is in the first position to press the microneedle device into the skin surface until the threshold application force is reached and the microneedle device is moved from the first position to the second position.

3. A method of applying a microneedle device to a skin surface, the method comprising:
   providing the applicator of claim 1;
   pressing the applicator in a direction substantially perpendicular to the microneedle device into the skin surface when the microneedle device is in the first position until the threshold application force is met or exceeded; and
   moving the microneedle device to the second position in response to meeting or exceeding the threshold application force.

4. The applicator of claim 1, wherein the connecting member has
   a first equilibrium position in which the microneedle device is in the first position, and
   a second equilibrium position in which the microneedle device is in the second position; and
   wherein the connecting member is configured to move to the second equilibrium position when the threshold application force is met or exceeded.

5. The applicator of claim 1, wherein the connecting member is coupled to the housing via a first hinge, and wherein the connecting member is coupled to the microneedle device via a second hinge.

6. The applicator of claim 1, wherein a first portion of the connecting member is coupled to the housing via a first hinge, and a second portion of the connecting member is coupled to the microneedle device via a second hinge.

7. The applicator of claim 5, wherein the connecting member pivots about the first hinge and the second hinge when the microneedle device is moved between the first position and the second position.

8. The applicator claim 5, wherein the first hinge and the second hinge are living hinges.

9. The applicator of claim 1, wherein the connecting member comprises a bifurcating spring.

10. The applicator of claim 1, wherein the threshold application force is a first threshold application force, and wherein the connecting member is configured to move the microneedle device to the first position when a second threshold application force is applied to the second side of the microneedle device in a direction oriented substantially perpendicularly with respect to the microneedle device.

11. The applicator of claim 10, wherein the second threshold application force is equal and opposite to the first threshold application force.

12. The applicator of claim 1, wherein the connecting member is further configured to move the microneedle device to the first position when the threshold application force is applied to the second side of the microneedle device in a direction oriented substantially perpendicularly with respect to the microneedle device.

13. The applicator of claim 1, further comprising a plunger movable with respect to the housing between a first position and a second position to move the microneedle device to the first position.

14. The applicator of claim 13, wherein the microneedle device is configured to move from its first position to its second position in a first direction, and wherein the plunger is configured to move from its first position to its second position in a second direction that is opposite the first direction and oriented substantially perpendicularly with respect to the microneedle device.

15. The method of claim 3, further comprising moving the microneedle device from the second position to the first position.

16. The method of claim 3, further comprising returning the microneedle device to the first position.

17. The method of claim 16, wherein the applicator further comprises a plunger movable with respect to the housing between a first position and a second position, and wherein returning the microneedle device to the first position includes moving the plunger from its first position to its second position.

18. The method of claim 16, wherein moving the microneedle device from the first position to the second position includes moving the microneedle device in a first direction oriented substantially perpendicularly with respect to the microneedle device, and wherein returning the microneedle device to the first position includes moving the microneedle device in a second direction that is opposite the first direction.

19. The method of claim 16, wherein the threshold application force is a first threshold application force, and wherein returning the microneedle device to the first position includes applying a second threshold application force to the second side of the microneedle device.

20. The method of claim 19, wherein the second threshold application force is equal and opposite to the first threshold application force.

* * * * *